(12) United States Patent
Nachabe et al.

(10) Patent No.: US 11,154,259 B2
(45) Date of Patent: Oct. 26, 2021

(54) CATHETER TYPE SELECTION

(71) Applicant: KONINKLIJKE PHILIPS N.V., Eindhoven (NL)

(72) Inventors: Rami Nachabe, Cincinnati, OH (US); Markus Johannes Harmen Den Hartog, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 278 days.

(21) Appl. No.: 16/307,985

(22) PCT Filed: Jun. 29, 2017

(86) PCT No.: PCT/EP2017/066179
§ 371 (c)(1),
(2) Date: Dec. 7, 2018

(87) PCT Pub. No.: WO2018/002250
PCT Pub. Date: Jan. 4, 2018

(65) Prior Publication Data
US 2019/0298278 A1    Oct. 3, 2019

Related U.S. Application Data

(60) Provisional application No. 62/356,580, filed on Jun. 30, 2016.

(30) Foreign Application Priority Data

Jul. 27, 2016  (EP) .................................. 16181370

(51) Int. Cl.
*A61B 6/12*   (2006.01)
*A61B 34/10*  (2016.01)
(Continued)

(52) U.S. Cl.
CPC ................ *A61B 6/12* (2013.01); *A61B 5/055* (2013.01); *A61B 5/6852* (2013.01); *A61B 6/032* (2013.01);
(Continued)

(58) Field of Classification Search
CPC ......... A61B 5/6852; A61B 6/12; A61B 6/504; A61B 34/10; A61B 2034/108; G01R 33/5635
See application file for complete search history.

(56) References Cited

U.S. PATENT DOCUMENTS

2006/0079759 A1   4/2006  Vaillant
2008/0160489 A1   7/2008  Bruijns
(Continued)

FOREIGN PATENT DOCUMENTS

CN    104095654 A    10/2014
WO    2006090324 A1   8/2006

OTHER PUBLICATIONS

Rahman, Sami U. et al, "Patient Specific Optimal Catheter Selection for right Coronary Artery", Medical Imaging 2011, Visualization, Image-Guided Procedures, and Modeling. vol. 7964, No. 1, pp. 1-7

*Primary Examiner* — Jason M Ip

(57) ABSTRACT

Methods, image processing system, and computer program elements are provided for algorithmically determining optimal catheter types for use in traversing a determined vascular path. The algorithmic determination uses geometric values obtained from angiogram imaging data and a database of available catheter types and corresponding geometric values for the available catheter types.

16 Claims, 6 Drawing Sheets

(51) Int. Cl.

| | | |
|---|---|---|
| *A61B 6/03* | (2006.01) | |
| *G01R 33/563* | (2006.01) | |
| *G16H 50/50* | (2018.01) | |
| *A61B 5/055* | (2006.01) | |
| *G16H 30/40* | (2018.01) | |
| *A61B 5/00* | (2006.01) | |
| *A61B 6/00* | (2006.01) | |
| *G09B 23/28* | (2006.01) | |
| *A61B 90/00* | (2016.01) | |

(52) U.S. Cl.
CPC ............ *A61B 6/4441* (2013.01); *A61B 34/10* (2016.02); *G01R 33/5635* (2013.01); *G09B 23/285* (2013.01); *G09B 23/286* (2013.01); *G16H 30/40* (2018.01); *G16H 50/50* (2018.01); *A61B 6/504* (2013.01); *A61B 2034/107* (2016.02); *A61B 2034/108* (2016.02); *A61B 2090/374* (2016.02); *A61B 2090/3762* (2016.02)

(56) References Cited

U.S. PATENT DOCUMENTS

| | | |
|---|---|---|
| 2008/0275467 A1 | 11/2008 | Liao |
| 2009/0182287 A1 | 7/2009 | Kassab |
| 2011/0295199 A1 | 12/2011 | Popovic |
| 2012/0014577 A1 | 1/2012 | Ferschel |
| 2014/0254906 A1 | 9/2014 | Poole |
| 2015/0011866 A1 | 1/2015 | Baumgartner |
| 2017/0079719 A1* | 3/2017 | Warner .................. A61B 5/055 |

* cited by examiner

CATHETER TYPE SELECTION

CROSS-REFERENCE TO PRIOR APPLICATIONS

This application is the U.S. National Phase application under 35 U.S.C. § 371 of International Application No. PCT/EP2017/066179, filed on Jun. 29, 2017, which claims the benefit of U.S. Provisional Patent Application No. 62/356,580, filed on Jun. 30, 2016 and European Patent Application No. 16181370.4, filed on Jul. 27, 2016. These applications are hereby incorporated by reference herein.

FIELD OF THE INVENTION

The technical field relates generally to catheter type selection and more particularly, but not exclusively, to catheter type selection for interventional vascular procedures.

BACKGROUND OF THE INVENTION

Interventional procedures in the vascular system of a mammal can require insertion of a catheter into specific arteries for therapeutic purposes such as drug injection into a feeding vessel to a cancer tumor, coiling a pseudo aneurysm, gel foaming a bleeding vessel etc. The vascular system is relatively complex with a dendritic branched network with each branch dimensions differing between patients. It may be difficult to sub select arteries due to complex curvature and tortuosity of each vessel. Several catheter shapes exist but choice of the correct or best catheter shape for a particular path is too dependent upon experience and personal choice. Furthermore, in the case of an error in selection, the consequences of a need to exchange between multiple catheters through the vessels can be damaging to lumen (vessel wall) and can cause blood thrombosis, itself possibly leading to life threatening emboli.

WO2006/090324 (Philips) relates to a method for the prediction of the course of a catheter between a given starting location (for example the incision where the catheter is introduced into the body) and a given target location (for example an aneurysm) in a modeled vessel system. The course of the catheter is described by a tubular object called "course tube", wherein said tube runs along an associated "course center line" leading from the starting location to the target location. The method comprises the determination of a path through the vessel system leading from the starting location to the target location, and the identification of an initial course center line with said path. If the vessel system is for example modeled by a tubular object with a center line, the path may follow said vessel center line. The method further comprises the adjustment of the aforementioned initial course center line in such a way that the course tube associated with this center line lies within the vessel system. This document further proposes the pre-molding, of the catheter in accordance with the predicted course. Time constraints and other practicalities may make individual tailoring of each catheter challenging.

One object of the present method, system and computer program is to select an elongate intravascular device, e.g. a (micro-)catheter, for a particular procedure and a particular patient. This facilitates the procedure (e.g. intervention) substantially, makes difficult cases treatable, and reduces the risk of complications.

SUMMARY OF THE INVENTION

Methods, image processing system, and computer program elements are provided for algorithmically determining optimal elongate intravascular device types using geometric values obtained from angiogram imaging data for use in traversing a determined vascular path and a database of available elongate intravascular device types and corresponding geometric values for the available elongate intravascular device types. In this way, one or more elongate intravascular device types can be optimally selected in the procedure planning phase, thereby reducing the risk of having to exchange catheters during the procedure.

The present disclosure provides an image processing system for determining at least one elongate intravascular device type for use in traversing a vascular path between a start point and a target destination in a vascular system, the image processing system comprising at least one processor configured to:

determine the vascular path based on angiogram imaging data of the vascular system from the start point to the target destination;

determine at least one geometric value of the vascular path at least at a junction where the vascular system has branches and the vascular path takes one of the branches of the vascular system;

determine at least one elongate intravascular device type suited to the at least one geometric value from a range of available catheter types stored in a database; and output an indication of the determined at least one elongate intravascular device type.

Based on the output, a medical professional is able to obtain the at least one elongate intravascular device type, which has been algorithmically determined as being suitable for the determined vascular path, for use in a medical procedure, e.g. interventional procedure.

The elongate intravascular device may be a catheter, a wire, a sheath, etc.

The at least one processor may be configured to determine a location for use of the determined at least one elongate intravascular device type along the vascular path. For example, a finish location for a distal end of each of the determined at least one elongate intravascular device type along the determined vascular path may be determined. The output may include an indication of the location for use. In this way, guidance is provided not only as to the optimal at least one elongate intravascular device type, but also as to the use thereof along the pathway.

The at least one processor may be configured to output the indication of the determined at least one elongate intravascular device type by overlaying, in at least one image for display corresponding to the angiogram imaging data, a graphical indication of the determined at least one elongate intravascular device type at the location for use. This provides an intuitive guidance output and can be used also in live tracking of an intervention procedure to guide where each of the at least one elongate intravascular device is to be utilized.

The at least one processor may be configured to use a model of the determined at least one elongate intravascular device as the graphical indication shown to scale and in situ in at least one image corresponding to the angiogram imaging data. Thus, the bends taken along the vascular path, the finishing point of the elongate intravascular device type along the vascular path and the scale of the elongate intravascular device type relative to vascular system can be assessed by a medical professional. The model may be stored in the database or in other memory.

The at least one determined elongate intravascular device type may be a plurality of determined elongate intravascular device types and a different graphical indication of each of the determined elongate intravascular device types is overlain in the at least one image. In this way, where the vascular path dictates a requirement for plural catheters to reach the target, guidance is provided as to each suitable elongate intravascular device.

The at least one processor may be configured to output an indication of a succession of elongate intravascular devices, particularly catheters. In this way, a sequence of the devices or catheters to be used along the vascular path can be determined and output so that the appropriate catheter types and their order of use can be algorithmically set.

The at least one geometric value may be the radius of curvature and/or angle of the vascular path at the junction. These parameters represent a shape of the junction and are important values for determining an appropriate shape of the elongate intravascular device for traversing the path.

The at least one processor may be configured to determine the at least one elongate intravascular device type for traversing the branch in the vascular system at the junction based on a comparison of the at least one geometric value and a corresponding geometric value of the available elongate intravascular device types stored in the database. A comparison of geometric values allows suitable elongate intravascular device shapes and sizes to be determined in a structured way. In particular, equivalence of the stored and angiogram determined geometric values may be determined by the comparison.

In an alternative or additional embodiment, the at least one processor is configured to determine the at least one elongate intravascular device type for traversing the branch in the vascular system at the junction based on a comparison of the at least one geometric value and a property of the available elongate intravascular device types stored in the database, wherein the property is indicative of a capability of the elongate intravascular device to traverse the branch in the vascular system. The property may be shape or material properties such as flexibility or elasticity. For example, each at least one geometric value such a radius of curvature and bend angle may correspond to particular requirement for material properties to traverse such a branch. Thus, the processor is configured to determine a suitable elongate intravascular device based on suitable material properties. Such material property requirements with respect to the at least one geometric value may be calculated or stored in a look-up table or may be part of the database. The processor may thus be configured to search or filter the database on the basis of thresholds of material property requirements. Additionally, the processor may be configured to search or filter the database on the basis of at least one required geometric value, e.g. outer diameter and shape (as defined by radius of curvature and/or angle) to determine at least one elongate intravascular device from the database suited to the vascular path.

The at least one processor may be configured to determine geometric values in the vascular path at each junction along the vascular path and in at least one segment between junctions. Thus, not only are the bends taken into account by the algorithm, but also the geometry of segments between the bends.

The geometric values may include diameter and/or cross-section of the at least one segment between junctions and the radius of curvature and/or angle of the path at the junctions. In this way, the actual minimum bore size of the vasculature along at least part of the vascular path can be determined and at least one elongate intravascular device along that path is chosen that fits within that path (or path portion).

The at least one processor may be configured to generate an image of the vascular path in the angiogram including segments between junctions at which the vascular path branches, and wherein the output includes a visually distinguishable indication of determined plural elongate intravascular device types at least in the image of the segments. The appropriate elongate intravascular device for each determined segment along a vascular path can be shown in a visually differentiable way to guide a medical profession both pre-planning and optionally by way of live tracking during a procedure.

The present disclosure further provides a system comprising the image processing system of any preceding claim and at least one of:

an imaging device for generating the angiogram imaging data;

the database;

at least one elongate intravascular device of the determined at least one elongate intravascular device type for use in a procedure.

The present disclosure further provides a computer implemented method for determining at least one elongate intravascular device type for use in traversing a vascular path between a start point and a target destination in a vascular system, the method comprising:

determining the vascular path based on angiogram imaging data of the vascular system from the start point to the target destination;

determining, based on the angiogram imaging data, at least one geometric value in the vascular path at least at a junction where the vascular system has branches and the vascular path takes one of the branches of the vascular system;

determining at least one elongate intravascular device type suited to the at least one geometric value from a range of available elongate intravascular device types stored in a database; and outputting an indication of the determined at least one elongate intravascular device type.

The method may implement any of the features of the image processing system described herein.

The present disclosure also provides a computer program element for controlling an image processing system as described above, which, when executed by the at least one processor, is adapted to configure the processor to performed the stated features or to perform the method features described herein.

Further, a computer readable medium is provided having stored the computer program element described herein.

These and other aspects of the invention will be apparent from and elucidated with reference to the embodiment(s) described hereinafter.

DESCRIPTION OF THE DRAWINGS

The exemplary embodiments will hereinafter be described in conjunction with the following drawing figures, wherein like numerals denote like elements, and wherein.

DETAILED DESCRIPTION

The following detailed description is merely exemplary in nature and is not intended to limit the application and uses. Furthermore, there is no intention to be bound by any expressed or implied theory presented in the preceding technical field, background, brief summary or the following detailed description. In the following description, catheters are described as the exemplary intravascular devices. However, other intravascular devices are possible such as sheaths and wires.

Precision delivery of drugs and other treatments by medical staff requires a catheter with an end located at the vascular site for drug delivery or treatment. Catheters or other intravascular devices are pushed or fed to the site, which can be considered a target destination or point in a vascular system of a mammal where the treatment is needed. Catheters when pushed or fed can themselves cause damage to the vascular vessels such as to lumen. Prior to a procedure, such as drug infusion, at least one angiogram is performed so that the medical staff can better understand the vascular system leading to the target destination. Medical staff will choose a catheter most suited to the vascular path between a designated starting or access point to the vascular system and the target destination or point. Choice of catheter from a range of catheters available may be critical in terms of the risks of damage by pushing or feeding the catheter to the target destination along a vascular path. Hitherto, a lot has depended upon medical staff experience.

The present disclosure provides an image processing system that is able to assist an operative in selecting an optimal catheter for use in traversing a given vascular pathway.

Figure 1:
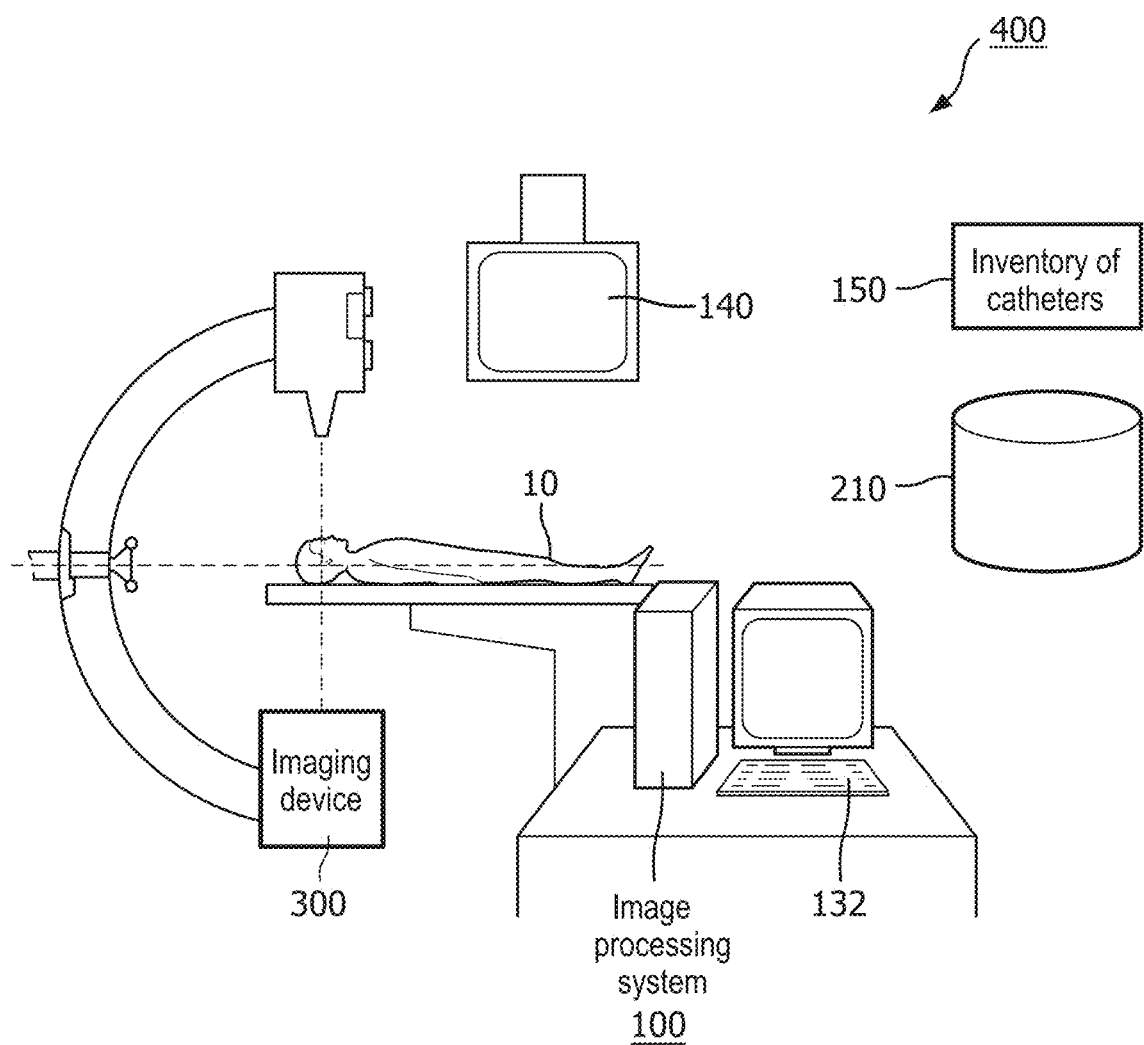
FIG. 1 is a schematic diagram of a system for obtaining angiogram imaging data, an image processing system and an inventory of available catheters.

FIG. 1 shows an imaging system comprising an image processing system 100. The image processing system 100 is for determining at least one catheter type 21, 31, 41, 51, 61 (shown in FIG. 4) for use in a vascular path 3 (shown in FIGS. 3 and 5) between a start point 2 and a target destination 4 in a vascular system 5.

In an exemplary embodiment, the imaging system 400 comprises an imaging device, such as an x-ray machine 300, disposed for taking images of a patient, optionally on a table 10. The image processing system 100, such as a general purpose computer, is operably connected to the imaging device 300 and processes the images from the imaging device 300. The processed images may be presented on a display unit 140 of the imaging system 400.

The imaging device 300 may comprise a magnetic resonance imaging (MRI) imaging device, a computed tomography (CT) imaging device. The imaging device 300 is capable, in combination with the image processing system 100, of obtaining angiogram images of a region of interest of the patient 10. The angiogram images may be 2 dimensional and/or 3 dimensional. Specific examples include 2 dimensional digital subtraction angiography (DSA) and/or 3 dimensional rotational angiography RA images. It is possible to combine two or more angiograms, consolidated by any known technique such as averaging.

The imaging system further comprises a database 210 storing information on available catheters. In particular, the database 210 relates catheter type identification numbers with geometric information for the catheter type and possibly material properties such as flexibility (or is inverse—stiffness) and/or elasticity. The geometric information in the database 210 may include information concerning the shape of various catheters, such as geometric information classifying the shape of shaped ends 23*a*, 33*a*, 43*a*, 53*a*, 63*a* of available catheters such as those shown in FIG. 4 and described further below. The classification of the shape may include information geometrically characterizing the bends. For example, the geometric information may include angle of bend in shaped ends 23*a*, . . . , radius of curvature (e.g. inner and outer radius of curvature), maximum diameter of the catheter 23, etc. The database 210 may be in communication with an electronic version of the inventory 150 of available catheters at a particular site so that determination of a suitable catheter for a particular path 3 (as described further below) can take into account catheters actually available to a surgeon at a particular site.

Figure 2:
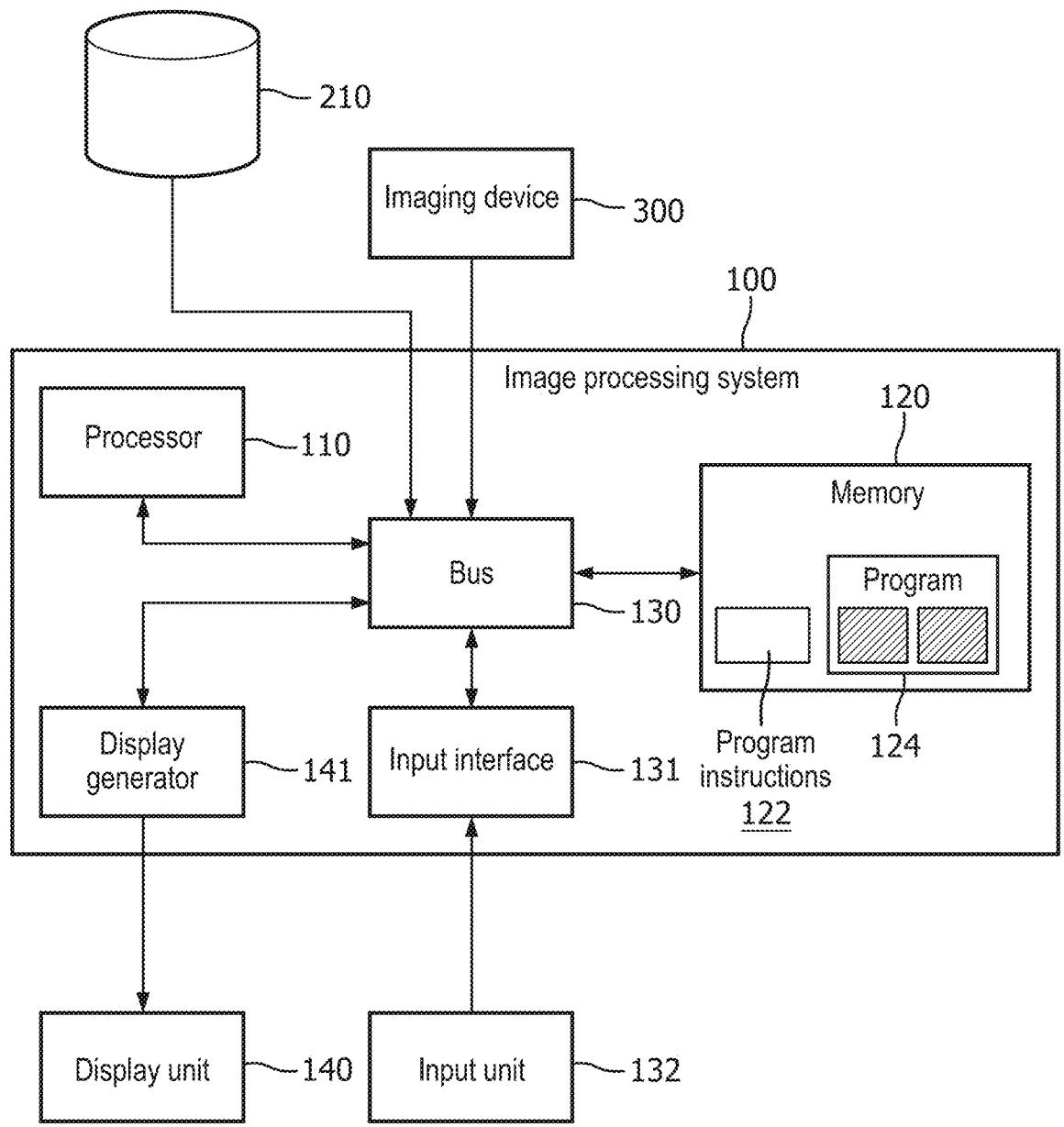
FIG. 2 is a schematic diagram of an image processing system according to an exemplary embodiment.

The image processing system 100 is shown in greater detail in FIG. 2. The image processing system comprises at least one processor 110. The processor 110 is operably connected to a memory 120. The processor 110 and the memory 120 may be connected through a bus 130. The processor 110 may be any device capable of executing program instructions, such as one or more microprocessors. The memory may be any volatile or non-volatile memory device, such as a removable disc, a hard drive, a CD, a Random Access Memory (RAM), a Read Only Memory (ROM), or the like. Moreover, the processor 110 may be embodied in a general purpose computer.

A display generator 141 is also operably connected to the processor 110 through the bus 130. The display generator 141 is configured to generate a display of images for the display unit 140 may be any monitor, screen, or the like suitable for presenting a graphical user interface (GUI) capable of presenting medical images.

The image processing system 100 further comprises an input interface 131 configured to receive and construe inputs from an input unit 132 of the imaging system 400. The input unit 132 could be any known input device such as a touchscreen device, a mouse, a keyboard, etc.

The image process system 100 has access to the database 210, optionally through the bus 130. Such access is required so that the processor 110 is able to compare geometric information for a determined path 3 for a catheter 21 with corresponding geometric (and other) information for available catheters stored in the database 210.

In the shown embodiment, the imaging device 300 is operably connected to the processor 110. The imaging device 300 obtains imaging data; which data is provided to the processor 110 for processing to create an angiogram of vascular system 5. The angiogram may then be presented on the display 140.

The memory 120 has encoded thereon, program instructions 122 which are executable by the processor 110 to process images from the imaging device 300. In addition to the program instructions 122 for processing the image for presentation on the display 140, a program of instructions 124 is also provided that performs a method of determining at least one catheter for use in a procedure requiring the at least one catheter to traverse the vascular system 5, as described further herein, particularly with reference to the flow chart of FIG. 6.

The image processing system 100 may be co-located with the imaging device 300 or remotely located or the image processing system 100 may take on a distributed architecture. As an example of the distributed architecture, at least one processor 110 may be located with the imaging device 300 to generate substantially live angiogram images for display on the display 140. Further, at least one processor 110 may be located elsewhere for pre-planning of a procedure that makes use of pre-existing angiogram images of the patient 10. The at least one processor 110 located elsewhere may be configured to execute the program of instructions 124 for determining at least one catheter for use in the interventional procedure requiring the at least one catheter to traverse the vascular system 5.

Referring to FIG. 1, the imaging system 400 further comprises a physical inventory of catheters 150 comprising a range of available catheters 21, . . . as shown in FIG. 4. A surgeon may use a catheter 21 from the inventory 150 in a procedure according to the catheter determined by the processor 110 as being optimally suitable for a given vasculature path 5.

In various embodiments, the processor 110, under the directions of the computer program 124, is configured to determine the vascular path 5 based on angiogram imaging data of the vascular system 5 from a start point 2 to a target destination 4. The vascular system 5 through the angiogram or angiograms will normally be assessed using known techniques or path predictors such as those described in published documents WO2006/090324, US2008/02755467. The processor 110 is configured to use a vessel segmentation algorithm to compute a vascular path 3 from the start point 2 to the target destination 5. In particular, vessel segmentation is performed on the angiogram imaging data to extract a model of the vascular system 5 according to one or more known techniques. The processor 110 is configured to determine the path 3 from the start point 2 to the target destination 5 along which at least one catheter 21 is to pass in order to reach the target destination. The path 2 may be determined using the model of the vascular system 5 and in an automated or semi-automated way based on known path finding algorithms. For example, the path finding algorithm could work on the basis of minimizing a number of branches traversed along the path 2, minimizing a distance of the path 2 or maximizing a total cross-sectional area of the vessels along the path 2 or combinations of these techniques. An operator may make use of the input unit 132 to adjust or redefine the suggested path 2 proposed according to the path finding algorithm. The path finding algorithm may indicate through the display unit 140 plural possible paths, normally depicted in an image of the path for medical staff so they can make a choice. However, normally there will only be one realistic vascular path to the target destination 4 from a readily available access point 2 as other paths are too tortuous and/or the dangers of thrombosis are too great or not justified.

A display unit, such as the display unit 140, may be configured to display the determined path 2, as explained below with reference to FIG. 3. The determined path 2 may be displayed as part of procedure planning and subsequently during the procedure in order to track the movement of the catheter 21.

The start position 2 and/or the target position 4 may be selected by an operator through the input unit 132. In a manual approach, an operator determines an access or start point 2 on the vascular system 5. This access point may be on the skin or internally within the patient as available, but will normally be an artery as the aim is to deliver drugs etc. to the target destination 4. Alternatively, in a more automated approach, a software algorithm may determine, from the angiogram taken of the vascular system 5 and using the path finding algorithm, that there are a number of access points with different vascular paths to the target destination 4. The target position 4 may also be algorithmically determined by the processor 110 using a disease finding program, which may also be guided by operator input through the input unit 132. Such a disease finding program may be able to locate probable tumors, vessel stenosis and other disease targets.

Accordingly, the processor 110 is configured so as to use a vascular vessel angiogram algorithm tool (e.g. including the above described segmentation algorithm and path finding algorithm) in order to determine a vascular path 3 from the start point or points 2 to the final destination 4 based on a full angiogram sequence obtained from the imaging device 300.

Figure 3:
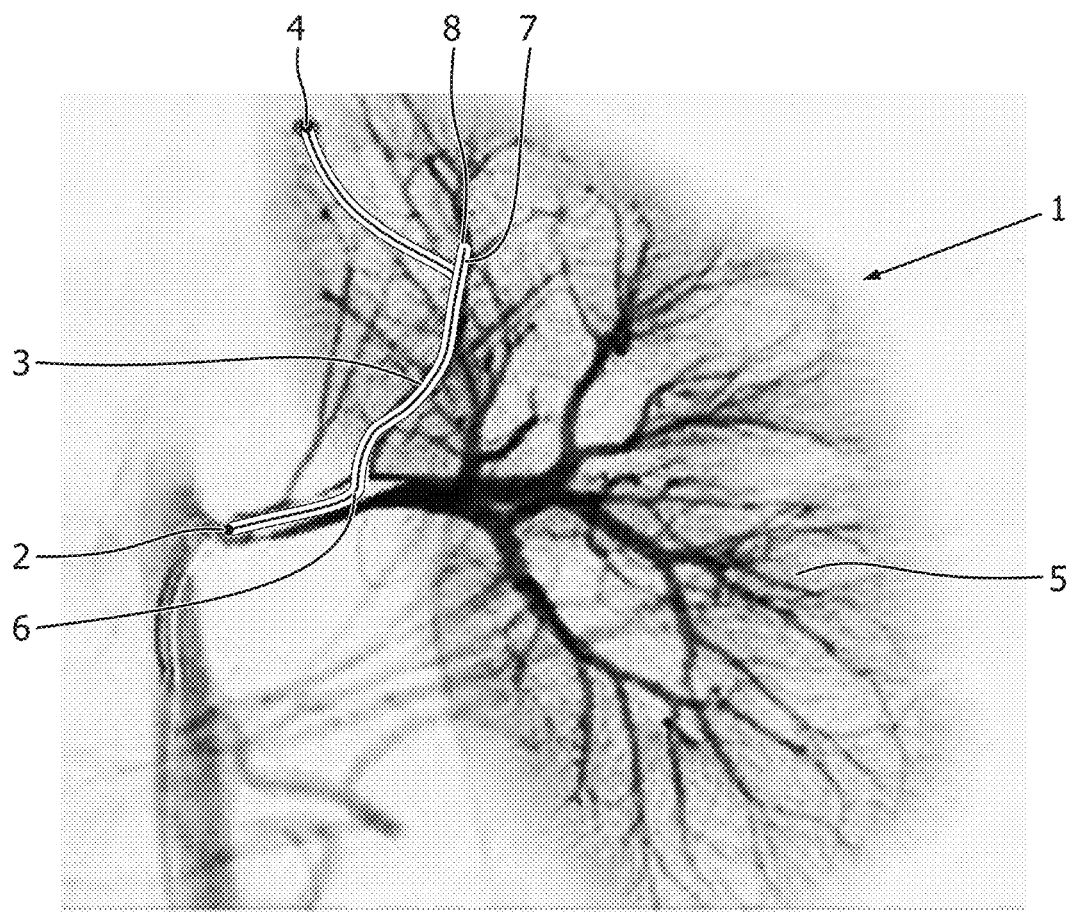
FIG. 3 is a renal angiogram image showing an access or start point and a target point or destination in a vascular system.
Figure 4A:
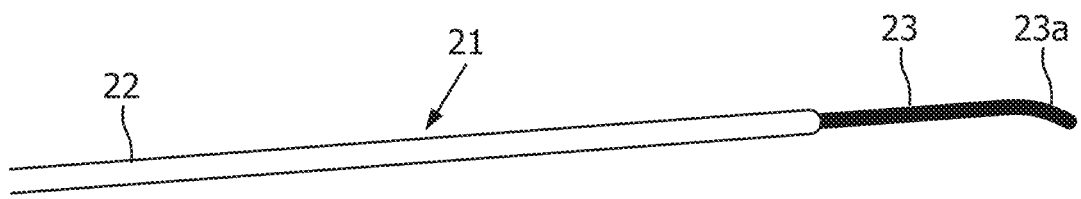
FIG. 4 provides depictions of some catheter shapes a) to e)
Figure 4B:
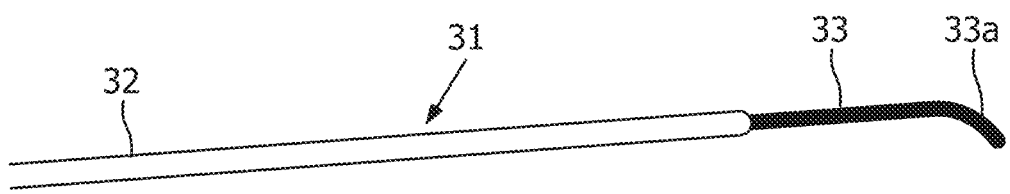
Figure 4C:
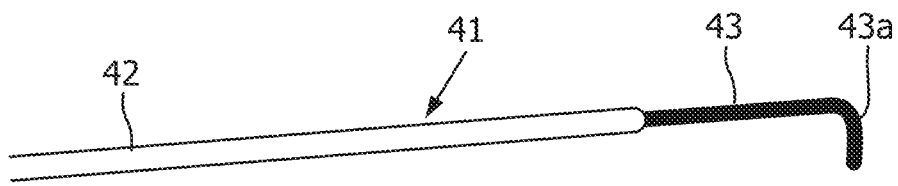
Figure 4D:
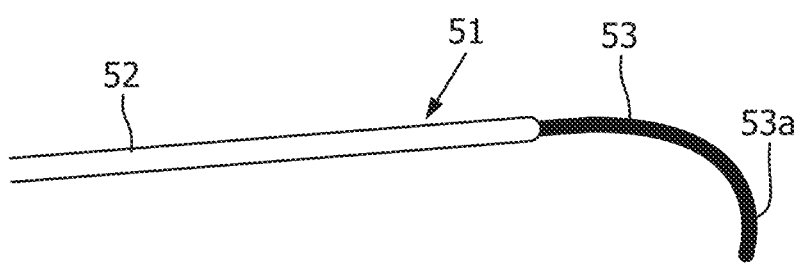
Figure 4E:
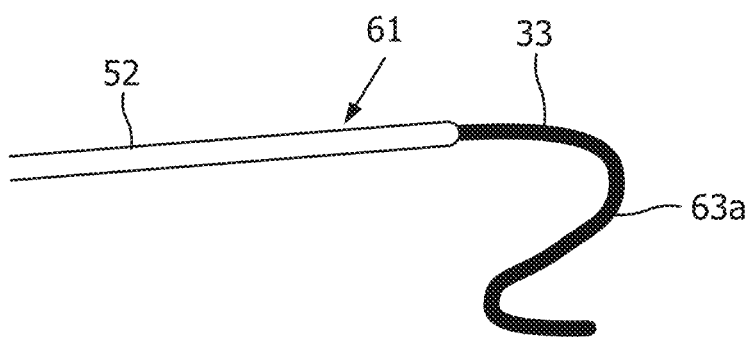

FIG. 3 is an image of a typical angiogram 1 of a vascular system 5. In the embodiment of FIG. 3, the angiogram is a renal angiogram. However, angiograms of other parts of the anatomy are included as providing possible vascular systems such as coronary angiograms, lower extremity angiograms, carotid angiograms, etc. and combinations thereof.

As shown in FIG. 3, the image includes an access point or starting position 2 (that has been determined or selected as described above), a destination position 4 (that has been determined or selected as described above) and a line showing a vascular path 3 (that has been determined as described above) to a target destination or position 4. The vascular path 3 indicates a path of travel for a catheter 21 prior to a surgical procedure and during live tracking of a catheter 21 during the surgical procedure. The determined vascular path 3 and the angiogram image are to be displayed in the same image for display, such as through the display unit 140.

Figure 5:
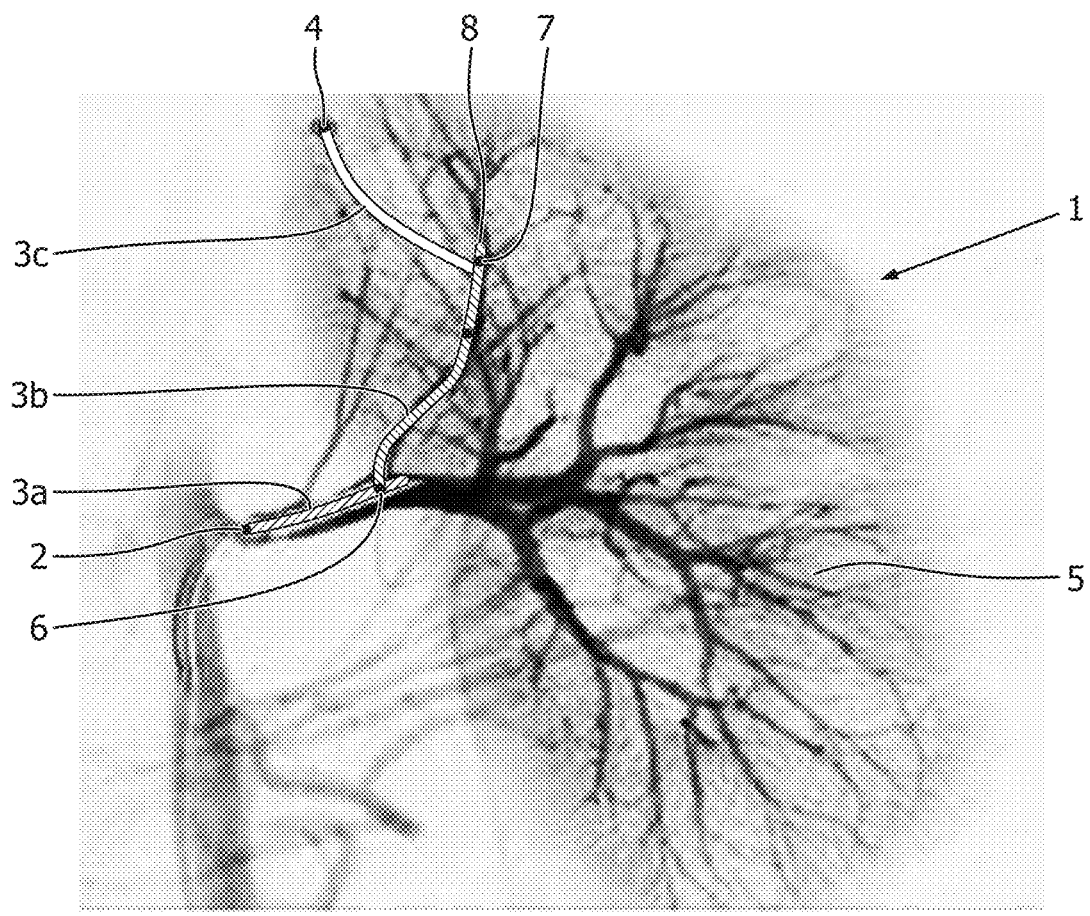
FIG. 5 is a similar renal angiogram to that depicted in FIG. 3 and illustrating sections of a vascular path in a vascular system accessed by different catheter shapes and configurations.

As can be seen, the vascular system 5 in general is a complex dendritic structure. The vascular path 3 passes generally from a main or trunk vessel into smaller, narrower branch vessels until the target destination or position 4 is reached. As will be appreciated, the target position 4 will have relatively small capillary sized vessels, which feed blood to tissue thereabout. The vascular path 3 as determined will traverse at least one branch in that vascular system 5. In FIG. 3, there are shown three branch points in the vascular path 3 at junctions 6, 7, 8. Between the branch points, there are vessel segments 3a, 3b and 3c as shown in FIG. 5.

In various embodiments, the processor 110 is configured to determine at least one geometric value in the vascular path 3 at least at a junction 6, 7, 8 where the vascular system has branches and the determined vascular path 3 takes one of the branches of the vascular system 5. To do so, the above described model of the vascular system 5, which has been constructed based on vessel segmentation of the angiogram imaging data, is used to extract geometric values concerning the vascular path 3. For example, at each junction 6, 7, 8 along the determined vascular path 3, a radius of curvature and/or angle of the determined path 3 may be algorithmically determined. Furthermore, vessel diameter or cross-sectional area data may be extracted for each segment 3a, 3b, 3c of the vessels between junctions 6, 7, 8. Such geometric data extraction can be performed using one or more known computer implemented quantitative vascular analysis (QVA) techniques operated by the processor 110.

In various embodiments, the processor 110 is configured to determine at least one catheter type suited to the at least one geometric value from a range of available catheter types stored in the database 210. The processor 110 may be configured to compare the geometric values extracted from the angiogram imaging data with corresponding geometric values of the available catheter types and/or at least one material property (such as elasticity and/or stiffness) stored in the database 210. A determination that the catheter type is suited for the determined path 3, or a portion thereof (particularly at least one of the junctions 6, 7, 8), may be made on the basis of equivalence (within a predetermined acceptable equivalence) of the geometric values. Additionally or alternatively, the processor 110 may be configured to look-up or determine suitable at least one material property for the catheter based on the at least one geometric value of the vascular path at least one junction 6, 7, 8. The processor 110 may be configured to compare the suitable at least one material property with corresponding at least one material property stored in the database 210 to determine the at least one suitable catheter type.

In an embodiment, the processor 110 may divide the path 3 into a plurality of portions, such as the segments 3a, 3b, 3c between the start position 2, the destination position 4 and the junctions 6, 7, 8. The processor 110 may be configured to determine at least one catheter type for each junction 6, 7, 8 and each segment 3a, 3b, 3c based on the comparison of geometric values determined from the angiogram imaging data and the corresponding geometric values obtained from the database 210 and/or from comparison of material properties as described above. The processor 110 is thus configured to compute shape equivalency (within a predetermined acceptable tolerance) between the determined path 3 and one or more catheter types for traversing that path 3.

Accordingly, when a vascular path 3 has been determined as described above, then a determination is made by the processor 110 of one or more catheter types matching the shape based on a consideration, in particular, of the radius of curvature and angle at each bifurcation 6, 7, 8 at branching nodes and junctions in the vascular system 5, is made. Each bifurcation 6, 7, 8 is the point in the vascular system where there is dendritic branching of the vascular system 5 so there are turns into one branch or another to provide the vascular path 3 between the access point 2 and the final destination 4.

It will be appreciated, although the term bifurcation is used relating to each node in which the vascular system 5 splits, there may be more than two child branches from the main branch. It is the actual detected vascular path 3 bifurcation split at a branching node or junction which is considered out of a number of potential splits at that junction. Normally, only one vascular path 3 will be considered segment for segment in terms of radius of curvature and angle at each bifurcation in the considered path 3.

Consideration in terms of geometric values or dimensions (radius of curvature/angle) of the determined vascular path 3 segment by segment or sections between bifurcation points 6, 7, 8 allows a determination of a most suitable catheter shape type for each segment in terms of the needs of the next bifurcation point 6, 7, 8. Each segment is the part of the vascular vessel between branching junctions 6, 7, 8 or nodes in the vascular system 5. In a branch network such as the vascular system 5 subsequent branches will tend to get narrower so the initial branch will be wider than the next branch and so on to the target destination 4.

FIG. 4 shows examples of catheter types 21, 31, 41, 51, 61 from which a selection can be made as to which catheter is to be used for a given procedure and a given determined vascular path 3. Catheters generally comprise a tube with a shaped end. FIG. 4 provides illustrative sub-FIGS. 4(*a*) to (*e*) of different catheter types. As can be seen, catheters, in addition to being distinguished by the bore width dimension of the tube, are categorized by the shape of their entry end or inlet tip. These shapes may have a shape memory to produce its characteristic shaped end 23, 33, 43, 53, 63. If several catheters are presented in concentric combination of descending tube bore sizes, then the widest will first present its shaped end with the other catheters withdrawn into the widest tube bore until needed. Such a catheter combination may have advantages and particularly may avoid a need to withdraw catheters between bifurcation nodes 6, 7, 8 and segments of the vascular path 3. A concentric catheter combination would be assembled of the necessary catheter types with shaped ends. This assembly could be prior to insertion and/or in situ so that one catheter is inserted along the path then, once past a bifurcation at a branching junction, another catheter is passed along and within the wider first catheter to extend beyond into the next segment of the vascular path towards and beyond to the next bifurcation at another junction or node and so on. This approach continues until the final destination 4 is reached by a combination of catheters. An initially formed concentric catheter combination would be fed or pushed along the path 3 from the access or start point 2 with a catheter shape for the next bifurcation 6, 7, 8 exposed and the others withdrawn. The catheter shape type best suited to that bifurcation will then engage that next bifurcation 6, 7, 8 to pass it. Such engagement may leave the shaped end of the catheter acting as a brace across the opened bifurcation or pass beyond the bifurcation, but in either event the next catheter in the concentric combination would then be pushed or fed forwards beyond the previous catheter along the path 3 to the next bifurcation 6, 7, 8.

FIG. 4(*a*) illustrates a catheter 21 with a fed tube 22 and a shaped end 23 comprising an inclined tip 23a of about 30 degrees to the tube 22. FIG. 4(*b*) illustrates a catheter 31 with a fed tube 32 and a shaped end 33 comprising an inclined tip 33a of about 60 degrees to the tube 32. FIG. 4(*c*) illustrates a catheter 41 with a fed tube 42 and a shaped end 43 comprising an inclined tip 43a of about 90 degrees to the tube 42. FIG. 4(*d*) illustrates a catheter 51 with a fed tube 52 and a shaped end 53 comprising a curved tip 53a, which subtends a quarter circle or arc. FIG. 4(*e*) illustrates a catheter 61 with a fed tube 62 and a shaped end 63 comprising an S shaped tip 63a. Each end 23, 33, 43, 53, 63 and particularly tips 23a, 33a, 43a, 53a, 63a will be best suited to different bifurcation configurations in terms of radius of curvature and/or angle and/or overall shape. Thus, once the vascular path 3 is determined in terms of bifurcations 6, 7, 8 then the best ends 23, 33, 43, 53, 63 will also be determined by the processor 110 for each bifurcation at a junction or node 6, 7, 8.

In various embodiments, the processor 110 is configured to output an indication of the determined at least one catheter type. Usually, the output is displayed on a display unit, such as the display unit 104. The indication of the determined at least one catheter type may comprise an indication of sequence of use when plural catheter types are determined for the procedure. In an exemplary embodiment, the output combines at least one image of the vasculature system 5 along the determined path 3 based on the angiogram imaging data and an overlaid graphic indicating the catheter type at each portion of the determined path 3. Where plural catheters are determined for the vascular path 3, a color coded graphic overlay may be used.

The output is described further with reference to the exemplary embodiment of FIG. 5.

FIG. 5 provides a further illustration of a similar angiogram to that depicted in FIG. 3 with the vascular path 3 between the start or access point 2 and the target destination 4 illustrated with segments 3a, 3b, 3c. Each segment 3a, 3b, 3c extends between the start/access point 2, bifurcation junctions or nodes 6, 7, 8 and the target destination 4 respectively. Each segment 3a, 3b, 3c has a designated catheter in terms of shape. An operator will be prompted by an indication in an angiogram image of a vascular system such as a color change in a marked path in the image to use a suggested catheter type for each segment 3a, 3b, 3c of the path 3.

In the path 3 depicted in FIG. 5, and as shown to an operator in an image, the various segments 3a, 3b, 3c may be shown as a color code. Each color code will overlay a respective segment 3a, 3b, 3c of the path in the image and that color code may correlate with a color code given to a particular catheter type. Each color code will correspond to a type of catheter and so will allow an operator such as a physician to know which catheter to use for each segment 3a, 3b, 3c of the vascular path 3. Typically, each color code will also suggest a catheter size that fits a vascular vessel consistent with the segment 3a, 3b, 3c of the path 3. Typically, the vascular vessel in segment 3a will be wider than segment 3b, which is wider than segment 3c and a cascading sequence of catheter types will be indicated as appropriate.

In addition to a color code, other visually identifiable differentiators may be utilized in the display of the angiogram imaging data to represent one or more particular catheter types.

Furthermore, a model of the catheter type could be utilized as part of the overlay. The model of the catheter type could be overlaid to scale and in location along the segment of vascular path. The model could be predetermined and stored in the database 210. For example, a wireframe model could be used, which may be included in the display of the angiogram imaging data in a color coded way where more than one catheter type is to be used.

In various embodiments, the processor 110 is configured to determine a location for use of the determined at least one catheter type along the vascular path 3. For example, the end location for each catheter type may be determined, which will usually be adjacent a junction 6, 7, 8 so that a smaller catheter type can then be telescoped from the end of the larger catheter type having an appropriately shaped end 23 for traversing the junction 6, 7, 8. The output may include a representation of the catheter (e.g. a model thereof as described above) overlaid along the vascular path showing the location at which the distal end of the catheter at a determined location along the vascular path 3 at which the catheter is to terminate.

In various embodiments, an order from the inventory 150 to a medical professional may be made in response to determination of at least one catheter type to be used in a procedure. The surgeon can subsequently use those catheters in the procedure. The order for at least one catheter from the inventory 150 may be collated and transmitted by the at least one processor 110 automatically in response to the determination of at least one catheter type.

In various embodiments, the processor 110 is configured to indicate a combination of the determined vascular path 3, angiogram imaging data and optionally also the overlay of at least one catheter type on the display unit 140 (through use of the display generator 141) during the procedure. Further, the processor 110 in combination with the imaging device 300 is configured to live track the movement of the catheter along the vascular path 3. In this way, guidance is provided as to each turn along the vascular system 5 that the one or more catheters must take to follow the determined vascular path 3. Further, guidance is provided as to a location at which the catheter is to terminate and optionally a nested catheter extended therefrom.

Figure 6:
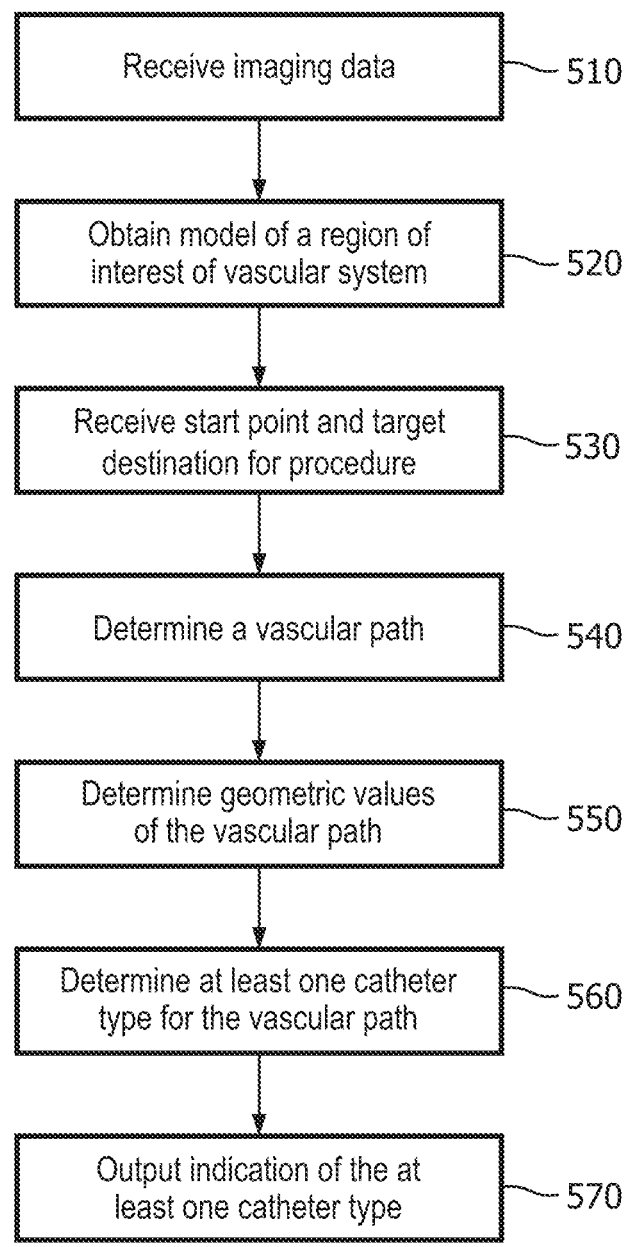
FIG. 6 is a flowchart according to an embodiment of the method described herein.

With reference now to FIG. 6, an exemplary method for determining at least one catheter type for use in an interventional procedure is disclosed. The method is computer implemented in that is carried out by at least one processor 110 directed by instructions of at least one computer program 124. The method is able to determine one or more suitable catheter types for use in traversing a vascular path 3 between a start point 2 and a target destination 4 in a vascular system 5.

In step 510, angiogram imaging data is received by the processor 110, optionally by way of a data interface unit (not shown) and the bus 130. The imaging data may be obtained previously by an imaging procedure using the imaging device 300, which is usually an X-ray based imaging device 300 such as a CT device.

In step 520, the angiogram imaging data is processed by the processor 110 to obtain a model of a region of interest of the vascular system 5. The model may be obtained using a vessel segmentation image processing technique on the angiogram imaging data. In step 530, the processor 110 receives a start point 2 and a target destination 4 for a catheter based procedure. Either or both of start and target positions 2, 4 may be user selected through a user input unit 132 or algorithmically determined by the processor 110.

In step 540, the processor 110 uses the model of the vascular system and the received start and target positions 2, 4 to determine a vascular path 3 as a recommendation for the passage of the catheter during the interventional procedure. The processor 110 may determine the vascular path 3 in an automated or semi-automated way (e.g. by taking into account user preferences or modifications from a user input unit 132). The processor 110 will make use of a path finding algorithm to determine the vascular path.

In step 550, the processor 110 determines, based on the angiogram imaging data, geometric values of the vascular path. The geometric values may include radius of curvature and/or angle of bends at junctions 6, 7, 8 and/or minimum bore size of each segment 3a, 3b, 3c between junctions 6, 7, 8 and/or minimum bore size of each junction 6,7,8. The geometric values are determined by the processor 110 using a quantitative vascular analysis technique based on the imaging data, usually as segmented by the vessel segmentation algorithm and possibly using the constructed model according to step 520.

In step 560, the processor 110 determines at least one catheter type suited to the determined vascular path 3 from a range of available catheter types stored in the database 210 based on the geometric values of the vascular path. In particular, the processor 110 may compare the determined geometric values for the vascular path with corresponding geometric values for catheter types stored in the database 210. Additionally or alternatively, the processor 110 may calculate or look-up one or more suitable material properties required for traversing a vascular path having the determined geometric values. The processor 110 may compare the suitable material properties (such as stiffness and/or elasticity) with corresponding material properties in the database 210 to determine at least one suitable catheter types. In this way, at least one catheter may be determined that is suited to the determined vascular path 3 based on equivalence (within a predetermined tolerance) of stored and determined properties such as geometric values and/or material properties.

In step 570, the processor 110 outputs an indication of the determined at least one catheter type. For example, the processor 110 operates in conjunction with the display generator 141, to produce images for display on the display unit 140. The image may combine the angiogram imaging data and a representation of the vascular path 3, along with a representation of the location of each catheter along the vascular path 3, which has been determined in step 560 based on the geometric values. The representation of the vascular path 3 and the representation of each catheter may be a model of each determined catheter in situ and to scale along the vascular path 3 in a display of the angiogram imaging data. The representation may be in the form of an overlay. Further, where more than one catheter has been determined for traversing the vascular path 3, a visually differential representation of each catheter is shown in the overlay, such as by way of color coding.

The method of FIG. 6 and described above may be part of a pre-procedure planning process. The determined catheter types can subsequently be obtained from the inventory 150. The output can be stored in the memory 120. The output can subsequently be used during live tracking of the procedure so that a medical professional can ascertain the vascular path and the finishing location of each catheter along the vascular path 3.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the disclosure in any way. Rather, the foregoing detailed description will provide those skilled in the art with a convenient road map for implementing the exemplary embodiment or exemplary embodiments. It should be understood that various changes can be made in the function and arrangement of elements without departing from the scope of the disclosure as set forth in the appended claims and the legal equivalents thereof.

For example, a set of catheter types could be supplied from the inventory with color or other coding consistent with the color codes displayed in an angiogram image of the vascular path in a vascular system or otherwise displayed. Catheters in each feed bore size range for each catheter type will mean these can be combined as concentric catheter combinations either during or prior to insertion into the vascular system.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An image processing apparatus for determining at least one elongate intravascular device type for use in traversing a vascular path between a start point and a target destination in a vascular system, wherein the vascular path comprises segments extending between the start point, junctions, and the target destination, respectively, the image processing apparatus comprising:
  a memory access interface configured to provide access to a database of available elongate intravascular device types; and
  at least one processor configured to:
    determine the vascular path based on angiogram imaging data of the vascular system from the start point to the target destination;
    determine at least one geometric value in the vascular path at least at a junction, wherein the vascular system comprises a plurality of branches and the vascular path takes one of the plurality of branches of the vascular system based on the angiogram imaging data;

access, via the memory access interface, the database of the available elongate intravascular device types;

determine a sequence of elongate intravascular device types, from the accessed available elongate intravascular device types, to be used along the vascular path and an order of use of the sequence of elongate intravascular device types, wherein each elongate intravascular device type in the sequence is designated to one of the segments; and output an indication of the sequence of elongate intravascular device types.

2. The image processing apparatus as claimed in claim 1, wherein the at least one processor is configured to determine a location for use of the sequence of elongate intravascular device types along the vascular path.

3. The image processing apparatus as claimed in claim 2, wherein the at least one processor is configured to output the indication of the sequence of elongate intravascular device types by overlaying in at least one image for display corresponding to the angiogram imaging data a graphical indication of each elongate intravascular device type in the sequence of elongate intravascular device types at the location for use.

4. The image processing apparatus as claimed in claim 3, wherein the at least one processor is configured to use models of each elongate intravascular device type in the sequence of elongate intravascular device types as the graphical indication shown to scale and in situ in at least one image corresponding to the angiogram imaging data.

5. The image processing apparatus as claimed in claim 1, wherein a different graphical indication of each elongate intravascular device type in the sequence of elongate intravascular device types is overlain in at least one image corresponding to the angiogram imaging data.

6. The image processing apparatus as claim 1, wherein the at least one processor is configured to output an indication of a succession of catheter types.

7. The image processing apparatus as claimed in claim 1, wherein the at least one geometric value is the radius of curvature and/or angle of the vascular path at the junction.

8. The image processing apparatus as claimed in claim 7, wherein the at least one processor is configured to determine the sequence of elongate intravascular device types for traversing a branch of the plurality of branches in the vascular system at the junction based on a comparison of the at least one geometric value and a corresponding geometric value of the available elongate intravascular device types stored in the database.

9. The image processing apparatus as claimed in claim 8, wherein the at least one processor is configured to determine geometric values in the vascular path at each junction along the vascular path and in at least one segment between the junctions.

10. The image processing apparatus as claimed in claim 9, wherein the geometric values include diameter; and/or cross-sectional area of the at least one segment between the junctions and a radius of curvature and/or angle of a path at the junctions.

11. The image processing apparatus as claimed in claim 10, wherein the at least one processor is configured to generate an image of the vascular path in the angiogram imaging data including segments between the junctions at which the vascular path branches, and wherein the output of the indication of the sequence of elongate intravascular device types includes a visually distinguishable indication of each elongate intravascular device type in the sequence of elongate intravascular device types at least in the image of the segments.

12. A system comprising the image processing apparatus of claim 1 and at least one of:
an imaging device configured to generate the angiogram imaging data;
the database; and
the elongate intravascular devices of the sequence of elongate intravascular device types for use in a procedure.

13. A computer implemented method for determining at least one elongate intravascular device type for use in traversing a vascular path between a start point and a target destination in a vascular system, wherein the vascular path comprises segments extending between the start point, junctions, and the target destination, respectively, the method comprising:
determining the vascular path based on angiogram imaging data of the vascular system from the start point to the target destination;
determining, based on the angiogram imaging data, at least one geometric value in the vascular path at least at a junction, wherein the vascular system has a plurality of branches and the vascular path takes one of the plurality of branches of the vascular system;
determining a sequence of elongate intravascular device types to be used along the vascular path and an order of use of the sequence of elongate intravascular device types, wherein each determined elongate intravascular device type is designated to one of the segments; and
outputting an indication of the sequence of elongate intravascular device types.

14. A non-transitory computer readable medium having stored thereon instructions that when executed by processing circuitry of an imaging apparatus causes the processing circuitry to:
determine a vascular path based on angiogram imaging data of a vascular system from a start point to a target destination;
determine, based on the angiogram imaging data, at least one geometric value in the vascular path at least at a junction, wherein the vascular system has a plurality of branches and the vascular path takes one of the plurality of branches of the vascular system;
determine a sequence of elongate intravascular device types to be used along the vascular path and an order of use of the sequence of elongate intravascular device types, wherein the vascular path comprises segments extending between the start point, junctions, and the target destination, respectively, and wherein each determined elongate intravascular device type is designated to one of the segments; and
output an indication of the determined sequence of elongate intravascular device types.

15. The computer implemented method as claimed in claim 13, comprising determining a location for use of the sequence of elongate intravascular device types along the vascular path.

16. The non-transitory computer readable medium as claimed in claim 14, comprising instructions that when executed by the processing circuitry cause the processing circuitry to determine a location for use of the sequence of elongate intravascular device types along the vascular path.

\* \* \* \* \*